(12) United States Patent
Chen et al.

(10) Patent No.: US 7,604,699 B2
(45) Date of Patent: *Oct. 20, 2009

(54) STENT COATING APPARATUS

(75) Inventors: Yung-Ming Chen, Cupertino, CA (US); Stephen James Guittard, San Jose, CA (US); Joe Broeckert, Onalaska, WI (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/016,669

(22) Filed: Jan. 18, 2008

(65) Prior Publication Data

US 2008/0141932 A1    Jun. 19, 2008

Related U.S. Application Data

(62) Division of application No. 10/322,255, filed on Dec. 17, 2002, now Pat. No. 7,338,557.

(51) Int. Cl.
    *B05B 7/00* (2006.01)
(52) U.S. Cl. .................. 118/300; 118/307; 118/320; 239/290; 239/296; 239/306; 239/398
(58) Field of Classification Search .......... 118/300, 118/319, 320, 313, 500, DIG. 11, 307; 239/290, 239/294, 296, 314, 8, 436; 427/2.24, 2.1, 427/2.25, 2.28, 425, 427.4, 427.5; 623/1.45, 623/920, 1.46, 1.47, 1.48, 283; 606/194
See application file for complete search history.

(56) References Cited

U.S. PATENT DOCUMENTS

| | | | |
|---|---|---|---|
| 2,647,017 A | 7/1953 | Coulliette | |
| 3,735,778 A | 5/1973 | Garnier | |
| 3,977,608 A | 8/1976 | Bullock | |
| 4,132,357 A | 1/1979 | Blackinton | |
| 4,146,900 A | 3/1979 | Arnold | |
| 4,733,665 A | 3/1988 | Palmaz | |
| 4,800,882 A | 1/1989 | Gianturco | |
| 4,886,062 A | 12/1989 | Wiktor | |
| 4,932,353 A | 6/1990 | Kawata et al. | |
| 4,967,606 A | 11/1990 | Wells et al. | |
| 5,015,505 A | 5/1991 | Cetnar | |
| 5,127,362 A | 7/1992 | Iwatsu et al. | |
| 5,190,219 A | 3/1993 | Copp, Jr. | |
| 5,201,466 A | 4/1993 | Hynds | |
| 5,225,750 A | 7/1993 | Higuchi et al. | |
| 5,368,560 A | 11/1994 | Rambo et al. | |
| 5,464,650 A | 11/1995 | Berg et al. | |
| 5,511,726 A | 4/1996 | Greenspan et al. | |
| 5,527,337 A | 6/1996 | Stack et al. | |
| 5,687,913 A | 11/1997 | Robisch et al. | |
| 5,700,286 A | 12/1997 | Tartaglia et al. | |
| 5,713,949 A | 2/1998 | Jayaraman | |
| 5,741,554 A | 4/1998 | Tisone | |
| 5,766,710 A | 6/1998 | Turnlund et al. | |

(Continued)

FOREIGN PATENT DOCUMENTS

EP    0 970 711    1/2000

(Continued)

OTHER PUBLICATIONS

Merriam-Webster's Collegiate Dictionary, Tenth Edition, 1998, p. 571.*

(Continued)

*Primary Examiner*—Yewebdar T Tadesse
(74) *Attorney, Agent, or Firm*—Squire, Sanders & Dempsey, L.L.P.

(57) ABSTRACT

A nozzle for use in a coating apparatus for the application of a coating substance to a stent is provided.

14 Claims, 4 Drawing Sheets

U.S. PATENT DOCUMENTS

| | | | |
|---|---|---|---|
| 5,769,883 | A | 6/1998 | Buscemi et al. |
| 5,824,056 | A | 10/1998 | Rosenberg |
| 5,837,313 | A | 11/1998 | Ding et al. |
| 5,843,172 | A | 12/1998 | Yan |
| 5,869,127 | A | 2/1999 | Zhong |
| 5,873,904 | A | 2/1999 | Ragheb et al. |
| 5,980,972 | A | 11/1999 | Ding |
| 5,984,449 | A | 11/1999 | Tajika et al. |
| 6,030,371 | A | 2/2000 | Pursley |
| 6,056,993 | A | 5/2000 | Leidner et al. |
| 6,068,202 | A | 5/2000 | Hynes et al. |
| 6,096,070 | A | 8/2000 | Ragheb et al. |
| 6,121,027 | A | 9/2000 | Clapper et al. |
| 6,132,809 | A | 10/2000 | Hynes et al. |
| 6,170,760 | B1 | 1/2001 | Bievenue et al. |
| 6,209,621 | B1 | 4/2001 | Treacy |
| 6,214,407 | B1 | 4/2001 | Laube et al. |
| 6,224,675 | B1 | 5/2001 | Prentice et al. |
| 6,273,706 | B1 | 8/2001 | Gunther |
| 6,345,553 | B1 | 2/2002 | Adler et al. |
| 6,395,326 | B1 | 5/2002 | Castro et al. |
| 6,462,284 | B1 | 10/2002 | Hashimoto |
| 6,488,773 | B1 | 12/2002 | Ehrhardt et al. |
| 6,491,666 | B1 | 12/2002 | Santini, Jr. et al. |
| 6,527,863 | B1 | 3/2003 | Pacetti et al. |
| 6,743,462 | B1 | 6/2004 | Pacetti |
| 6,811,805 | B2 | 11/2004 | Gilliard et al. |
| 7,087,115 | B1 * | 8/2006 | Moein .................. 118/300 |

FOREIGN PATENT DOCUMENTS

| | | |
|---|---|---|
| WO | WO 98/23228 | 6/1998 |
| WO | WO 01/45763 | 6/2001 |
| WO | WO 01/52772 | 7/2001 |
| WO | WO 2007098884 A1 * | 9/2007 |

OTHER PUBLICATIONS

"780S Series Spray Valves Valvemate™ 7040 Controller", Operating Manual, EFD Inc., 2003, (24 pgs).

"Impulse Jetting: About Us," http://www.impulsejetting.com/about.html, printed Dec. 18, 2000 (1 page).

"Impulse Jetting: Our Technology," http://www.impulsejetting.com/tech1.html, printed Dec. 18, 2000 (1 page).

Consistent, Precise spray valve system, EFD Inc., 2004 (2 pages).

Trident, Inc., http://www.tridetintl.com/subbody.html, printed Dec. 18, 2000 (4 pages).

World Precision Instruments, Inc., "Nanoliter 2000," http://www.wpi-europe.com/pumps/Nanoliter_Injector.html, printed Sep. 30, 2002 (4 pages).

World Precision Instruments, Inc., "Nonolite Injector," http://www.wpiinc.com/WPI_Web/Pumps/Nanoliter_Injector.html, printed Sep. 30, 2002 (3 pages).

World Precision Instruments, Inc., "Pneumatic PicoPumps," htttp://www.wpi-europe.com/pumps/Pneumatic_PicoPumps.html, printed Sep. 30, 2002 (7 pages).

World Precision Instruments, Inc., "Pneumatic PicoPumps," http://www.wpiinc.com/WPI_Web/Pumps/Pneumatic_PicoPumps.html, printed Sep. 30, 2002 (6 pages).

World Precision Instruments, Inc., http://www.wpiinc.com/WPI_Web/Pumps/pneumatic_Fig.gif, printed Sep. 30, 2002 (1 page).

Merriam-Webster's Dictionary (Tenth Edition), p. 1359.

* cited by examiner

STENT COATING APPARATUS

This application is a divisional of U.S. patent application Ser. No. 10/322,255, filed Dec. 17, 2002 now U.S. Pat. No. 7,338,557, the entire disclosure of which is incorporated herein by reference.

TECHNICAL FIELD

This invention relates to an apparatus used in the process of coating a stent, and more particularly provides a nozzle for use in drug eluting stent spray coating.

BACKGROUND

Blood vessel occlusions are commonly treated by mechanically enhancing blood flow in the affected vessels, such as by employing a stent. Stents act as scaffolding, functioning to physically hold open and, if desired, to expand the wall of affected vessels. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Giant-urco, and U.S. Pat. No. 4,886,062 issued to Wiktor.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by spraying the composition onto the stent. The solvent is allowed to evaporate, leaving on the stent surfaces a coating of the polymer and the therapeutic substance impregnated in the polymer.

A shortcoming of the above-described method of medicating a stent is the potential for coating defects and the lack of uniformity of the amount of composition material sprayed onto stents. While some coating defects can be minimized by adjusting the coating parameters, other defects occur due the shot to shot variation leading to excess composition being sprayed onto the stent. One cause of this shot to shot variation is the type of spray coater used. For example, a conventional EFD N1537 (EFD Inc. East Providence R.I.) spray coater uses a valve mechanism to dispense fluid and is most suitable for dispensing large amounts of composition (i.e., grams) and not small amounts (e.g., milligrams per spray cycle) as used in stent coating applications. Accordingly, conventional spray coaters tend to spray excess coating onto stents, which may stick to the stent, thereby leaving excess coating as clumps or pools on the struts or webbing between the struts.

Accordingly, a new nozzle for spraying coating is needed to minimize coating defects.

SUMMARY

The present invention is generally directed to a stent coating apparatus. In aspects of the present invention, the apparatus includes a stent coating composition reservoir containing a stent coating composition, a pump capable of dispensing the stent coating composition from the reservoir, an atomizer capable of atomizing the stent coating composition, and a nozzle assembly in communication with the atomizer, the nozzle assembly having a needle in fluid communication with the reservoir for dispensing the composition onto a stent from the reservoir.

In detailed aspects of the present invention, the nozzle assembly enables external atomization of the coating composition. In other detailed aspects, the nozzle assembly enables internal atomization of the coating composition.

In further aspects of the present invention, the nozzle assembly further includes, a needle centering body, the needle disposed in the needle centering body, and a chamber coupled to the needle centering body, the chamber having an inlet in fluid communication with the atomizer and capable of receiving gas from the atomizer for atomizing the composition as the composition is dispensed from the needle on to a stent. In still further aspects, the nozzle assembly further includes, a coupling element attached to the needle centering body, the coupling element having an inlet in fluid communication with the pump, and wherein the needle is in fluid communication with the coupling element and receives the coating composition from the coupling element through a hollow interior of the needle.

The features and advantages of the invention will be more readily understood from the following detailed description which should be read in conjunction with the accompanying drawings.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION

Figure 1:
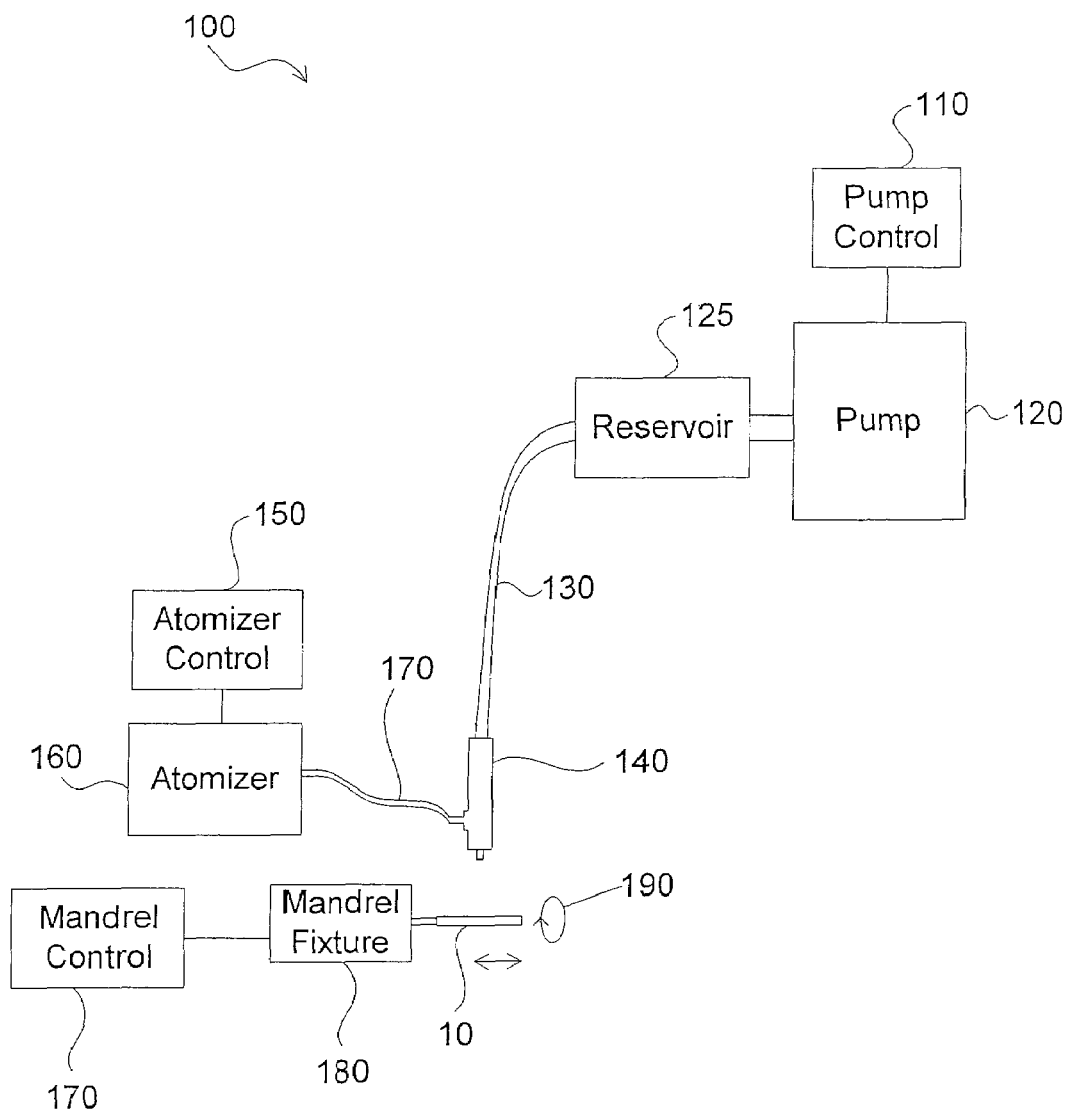
FIG. 1 is a block diagram illustrating a coating system for coating a stent with a composition.

FIG. 1 is a block diagram illustrating a coating system 100 for coating a stent 10 with a composition. The coating system 100 comprises a pump 120; a pump control 110; a reservoir 125; a nozzle assembly 140; an atomizer 160; an atomizer control 150; a mandrel fixture 180 and a mandrel fixture control 170. The pump control 110 is communicatively coupled to the pump 120 and controls the amount of fluid (also referred to interchangeably as coating substance or composition) dispensed by the pump 120 from the reservoir 125. The pump control 110 may include mechanical and/ or electrical control mechanisms. In an embodiment of the invention, the pump control 110 is integrated with the pump 120.

The pump 120 pumps fluid from the reservoir 125, for coating the stent 10, to the nozzle assembly 140 via a tubing 130. The pump 120 may pump the fluid from the reservoir 125 at a rate of 0.15 cc/min, for example. In one embodiment of the invention, the pump 120 includes a syringe pump. In another embodiment of the invention, the pump 120 includes a gear pump. It will be appreciated that the pump 120 can comprise other types of pumps and/or combinations of pumps such as a positive displacement pump or a green pump.

The coating substance can include a solvent and a polymer dissolved in the solvent and optionally a therapeutic substance or a drug added thereto. Representative examples of polymers that can be used to coat a stent include ethylene vinyl alcohol copolymer (commonly known by the generic name EVOH or by the trade name EVAL); poly(hydroxyvalerate); poly(L-lactic acid); polycaprolactone; poly(lactide-co-glycolide); poly(glycerol-sebacate); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrilestyrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Examples of solvents include, but are not limited to, dimethylsulfoxide, chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methylpyrrolidinone, toluene, and mixtures and combinations thereof.

The therapeutic substance or drug can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COS-MEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, dexamethasone, and rapamycin.

Figure 2:
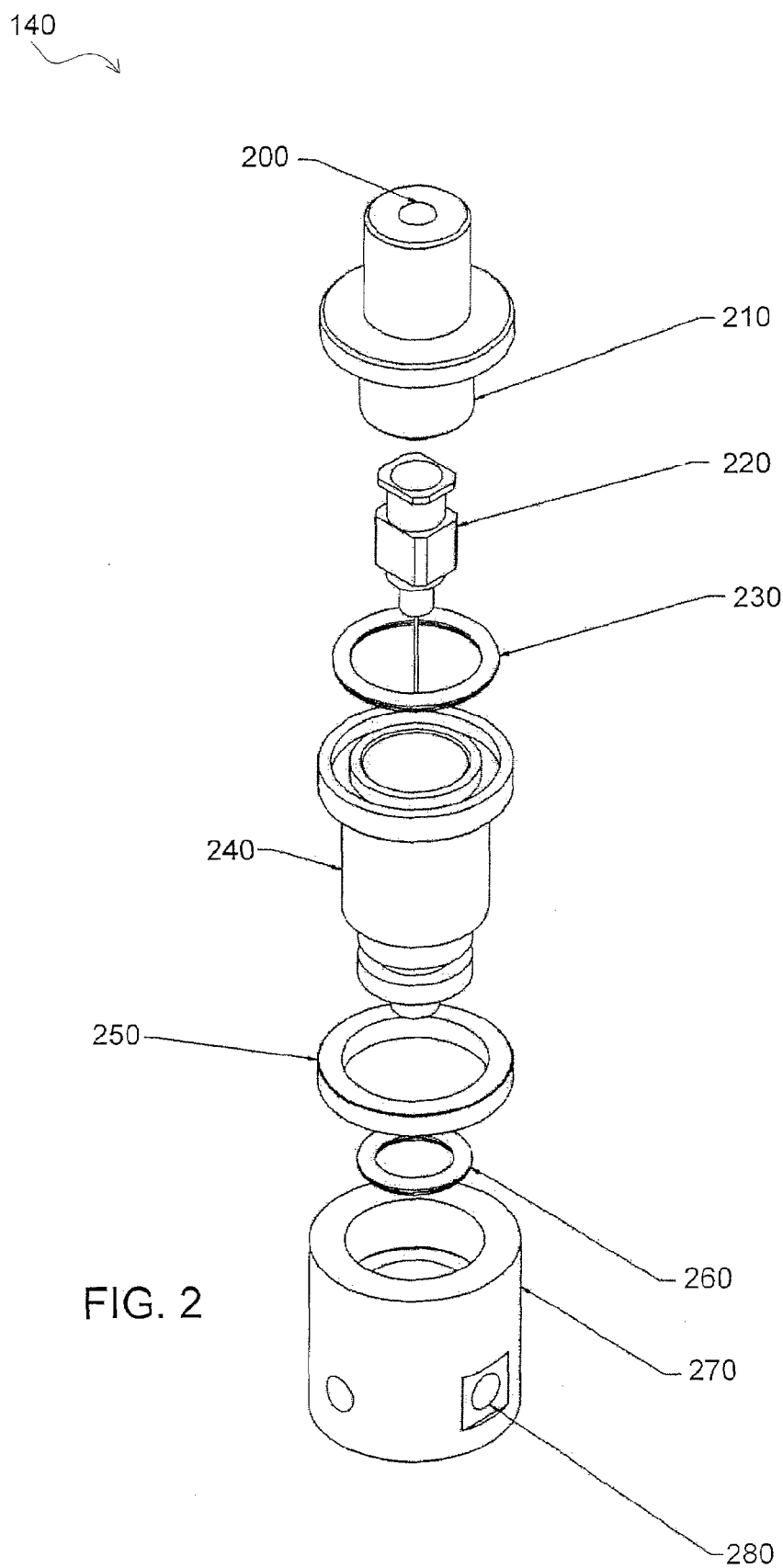
FIG. 2 is a disassembled perspective view illustrating the nozzle assembly of the coating system of FIG. 1 in accordance with an embodiment of the invention.

The atomizer 160 supplies high-pressure air to the nozzle assembly 140 via a tubing 170 coupled to an air inlet 280 (FIG. 2). This high-pressure air is used to atomize the composition dispensed from the nozzle assembly 140 onto the stent 10, as will be discussed in further detail in conjunction with FIG. 3 and FIG. 4. The atomizer control 150 is communicatively coupled to the atomizer 160 and controls the pressure of the air dispensed from the atomizer 160 to the nozzle assembly 140. The atomizer control 150 can include electrical mechanisms, mechanical mechanisms, or a combination thereof to control the atomizer 160. In an embodiment of the invention, the atomizer control 150 and the atomizer 160 can be integrated into a single device.

The mandrel fixture 180 supports the stent 10 during a coating application process. In addition, the mandrel fixture 180 can include an engine so as to provide rotational motion about the longitudinal axis of the stent 10, as depicted by the arrow 190, during the coating process. Another motor can also be provided for moving the stent 10 in a linear direction, back and forth. The mandrel control 170 is communicatively coupled to the mandrel fixture 180 and controls movement of the stent 10. The type of stent that can be crimped on the mandrel fixture 180 is not of critical significance. The term stent is broadly intended to include self- and balloon-type expandable stents as well as stent-grafts.

The nozzle assembly 140, as will be discussed in further detail in conjunction with FIG. 2, receives the coating composition from the reservoir 125 via the tubing 130. In addition, the nozzle assembly 140 receives high-pressure air from the atomizer 160. During a stent coating application process, the nozzle assembly 140 dispenses composition onto stent 10. During the dispensing, high-pressure air from the atomizer 160 atomizes the composition, leading to a more uniform distribution on the stent 10.

It will be appreciated that the multiple control devices, i.e., the pump control 110, atomizer control 150, and mandrel control 170 can be combined into a single control device to simplify setting parameters for an operator.

FIG. 2 is a disassembled perspective view illustrating the nozzle assembly 140 of the coating system 100 in accordance with an embodiment of the invention. The nozzle assembly 140 includes a coupling 210 having a fluid inlet 200; a hypodermic needle 220, two O-rings 230 and 260; a needle centering body 240; a needle height locking ring 250; and an air chamber 270 having an air inlet 280. The coupling 210 is in liquid communication with the reservoir 125 via the tubing 130 that is coupled to the fluid inlet 200. The coupling 210 receives the composition from the reservoir 125 for coating the stent 10. In an alternative embodiment of the invention, the nozzle assembly 140 includes a barrel connection, which is coupled to a barrel that dispenses fluid, in place of the coupling 210. In this alternative embodiment, the amount of fluid dispensed is controlled by a valve mechanism in conjunction with variable air pressure in the barrel and/or in the needle 220.

The hypodermic needle 220 is in liquid communication with the coupling 210 and receives the fluid for coating the stent 10 from the coupling 210. In an embodiment of the invention, the hypodermic needle 220 includes a 28 gauge needle. In an alternative embodiment of the invention, the nozzle assembly 140 includes a hypotube in place of the hypodermic needle 220. The O-ring 230 is located between the coupling 210 and the needle centering body 240 and forms a tight seal there between.

The needle centering body 240 securely centers the hypodermic needle 220 within the nozzle assembly 140. A portion of the needle centering body 240 is located within the air chamber 270 so as to form an air cavity for receiving air from the atomizer 160 via the air inlet 280 and exiting via an air outlet 300 (FIG. 3), as will be discussed in further detail in conjunction with FIG. 3 and FIG. 4. In an alternative embodiment of the invention, the air chamber 270 has a plurality of air inlets for receiving air from the atomizer 160.

In an embodiment of the invention, both the needle centering body 240 and the air chamber 270 have surfaces that are threaded, thereby enabling them to be coupled together at variable positions so that the tip of the hypodermic needle 220 can extend at variable lengths from the air chamber 270, as will be discussed in further detail in conjunction with FIG. 3 and FIG. 4. The needle height lock ring 250 locks the air chamber 270 and the needle centering body 240 securely together so as to prevent movement relative to each other during a spray coating process. The O-ring 260 is located between the air chamber 270 and the needle centering body 240 and forms a secure seal there between to prevent pressurized air escaping there from.

Figure 3:
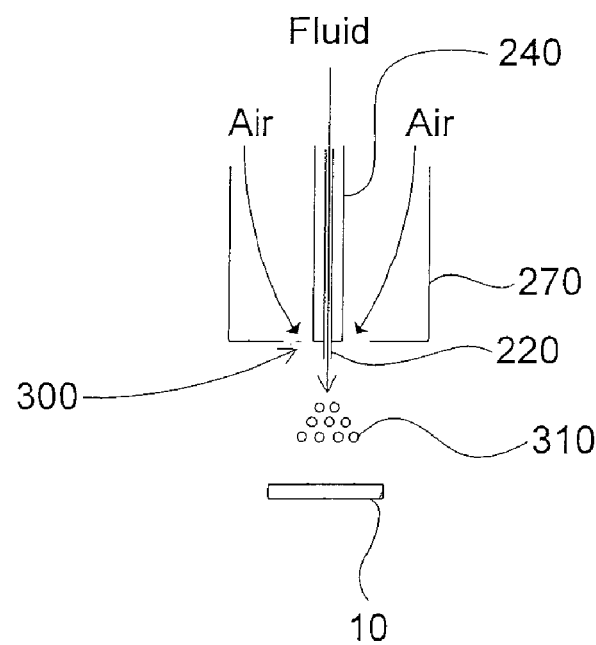
FIG. 3 is a schematic cross section illustrating a portion of the nozzle assembly with the hypodermic needle at a first position for external mixing.

FIG. 3 is a cross section illustrating a portion of the nozzle assembly 140 with the hypodermic needle 220 at a first position for external mixing. Air from the atomizer 160, via the air inlet 280, flows out of the cavity formed by the needle centering body 240 and the air chamber 270 via the air outlet 300. The atomizer 160 atomizes the fluid dispensed from the hypodermic needle 220 into atomized droplets, such as droplet 310 (not to scale), so that the fluid more evenly coats the stent 10. In one embodiment of the invention, the air outlet 300 is an annular aperture that circumscribes the needle 220 orifice.

Generally, smaller atomized droplets, e.g., a fine mist, is preferable to large droplets so as to ensure an even coating on the stent 10. Droplet size is directly proportional to the diameter of the hypodermic needle 220 orifice. Accordingly, a smaller needle orifice is superior for atomization than a larger diameter nozzle as used conventionally. More specifically, the standard median droplet diameter $$SMD \propto diameter_o U_R \frac{Mass_{fluid}}{Mass_{air}}, \text{ wherein } U_R = \frac{Velocity_{fluid}}{Velocity_{air}},$$

and wherein $diameter_o$ is the diameter of the needle 220 orifice. Accordingly, in addition to a small needle diameter, high air velocity and less fluid increases atomization of the fluid and therefore increases the even coating of the stent 10 with the fluid. Conventional nozzle assemblies that are designed to dispense grams of fluid per shot generally dispense large and uneven amounts of fluid per shot and so do not always enable adequate atomization. In contrast, the hypodermic needle 220 can dispense small uniform amounts of fluids via a small diameter orifice, thereby enabling adequate atomization of the fluid to ensure even coating of the stent 10. Another advantage of the hypodermic needle 220 is that it is disposable. Accordingly, the nozzle assembly 140 can be used for dispensing different fluids without worry of cross contamination by simply replacing the hypodermic needle 220 with a new needle.

The hypodermic needle 220, in the embodiment illustrated in FIG. 3, extends outward from the nozzle assembly 140, or, more specifically, extends downward from the air chamber 270, thereby enabling external mixing of the air from the atomizer 160 with the fluid dispensed from the hypodermic needle 220. In an exemplary embodiment of the invention, the hypodermic needle 220 can extend up to 2 cm from the air chamber 270. The distance that the needle 220 protrudes should not hinder the atomization of the composition. In one embodiment, the distance that the needle 220 protrudes is adjustable.

Figure 4:
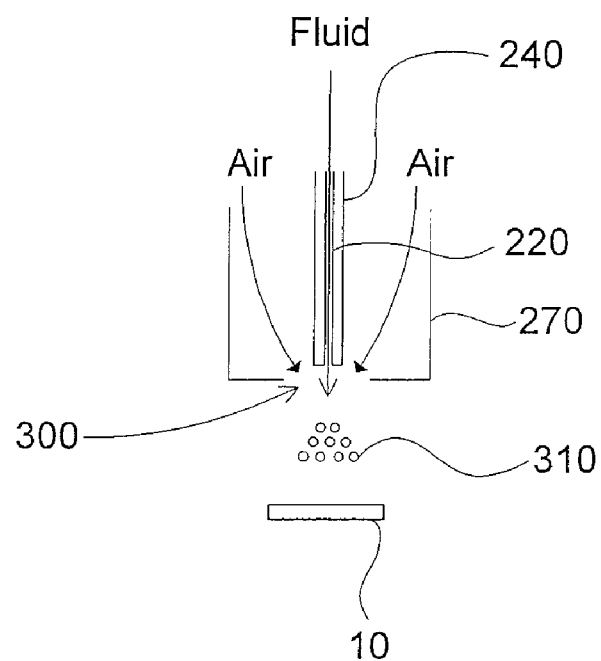
FIG. 4 is a schematic cross section illustrating a portion of the nozzle assembly with the hypodermic needle at a second position for internal mixing.

FIG. 4 is a cross section illustrating a portion the nozzle assembly 140 with the hypodermic needle 220 at a second position for internal mixing. Air from the atomizer 160, via the air inlet 280, flows out of the cavity formed by the needle centering body 240 and the air chamber 270 via the air outlet 300. The atomizer 160 atomizes the fluid dispensed from the hypodermic needle 220 into atomized droplets, such as droplet 310 (not to scale), so that the fluid more evenly coats the stent 10. The atomization, in this embodiment, is done within the air chamber 270 (i.e., internal mixing).

Figure 5:
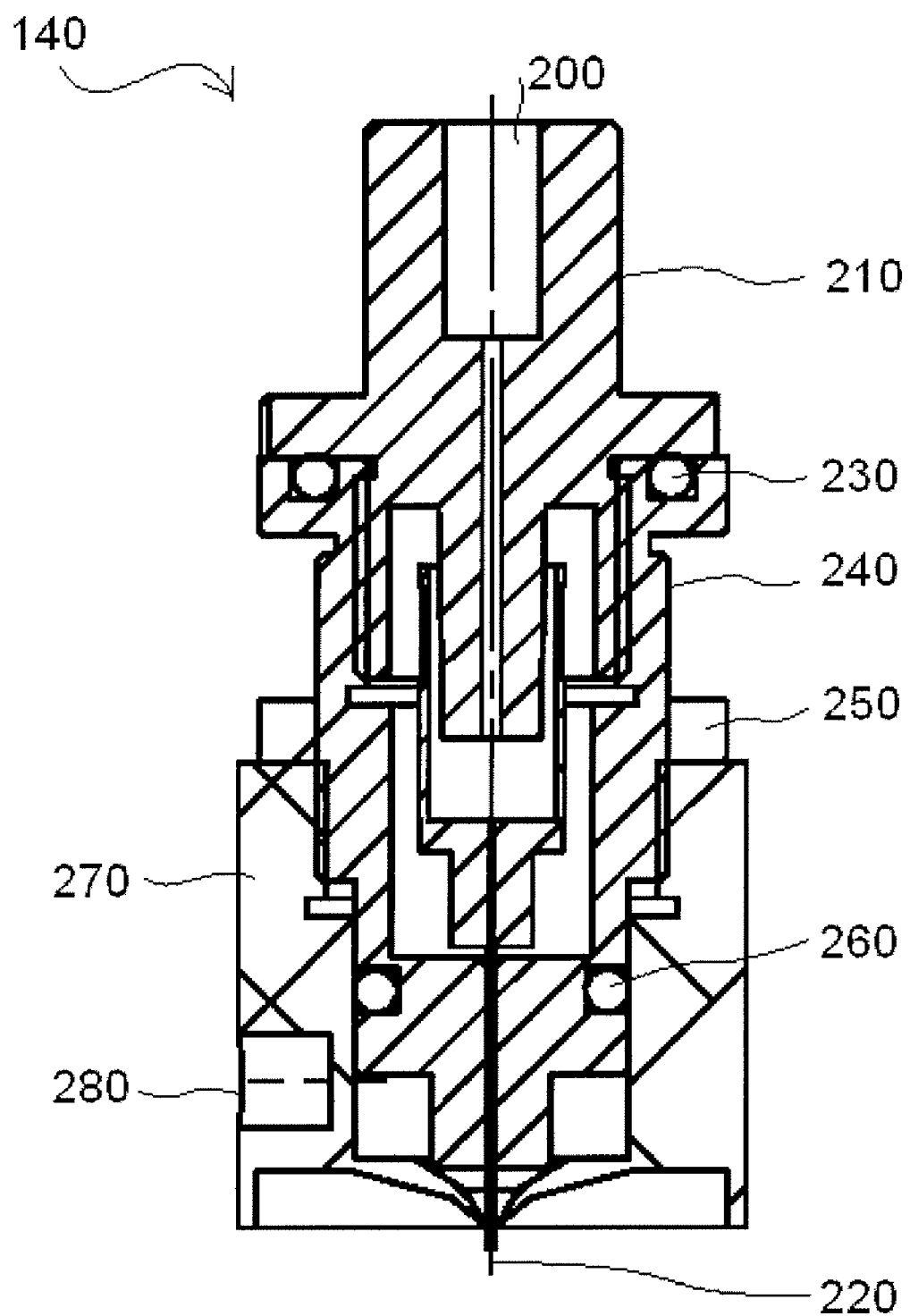
FIG. 5 is a cross section illustrating one embodiment of the nozzle assembly.

FIG. 5 is a cross section illustrating the nozzle assembly 140. Composition is fed into the fluid inlet 200 of the coupling 210. The composition flows into the needle 220 and then exits the nozzle assembly 140. The atomizer 160 supplies air to the air chamber 270 via the air inlet 280. The air supplied by the atomizer 160 atomizes composition as it exits the needle 220.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent coating apparatus, comprising:
   a stent coating composition reservoir containing a stent coating composition;
   a pump capable of dispensing the stent coating composition from the reservoir;
   an atomizer capable of atomizing the stent coating composition; and
   a nozzle assembly in communication with the atomizer, the nozzle assembly having a needle in fluid communication with the reservoir for dispensing the composition onto a stent from the reservoir, wherein the needle is a hypotube or a hypodermic needle.

2. The apparatus of claim 1, further comprising a stent fixture capable of securely supporting a stent during a coating process.

3. The apparatus of claim 2, wherein the stent fixture is further capable of rotating or translating the stent during a coating process.

4. The apparatus of claim 1, wherein the nozzle assembly enables external atomization of the coating composition.

5. The apparatus of claim 1, wherein the nozzle assembly enables internal atomization of the coating composition.

6. The apparatus of claim 1, wherein a segment of the needle protrudes out from the nozzle assembly.

7. The apparatus of claim 6, wherein the length of the segment that protrudes out from the nozzle assembly can be adjusted by a user.

8. The apparatus of claim 1, wherein the nozzle assembly includes an air chamber in fluid communication with the atomizer and capable of receiving air for atomizing the composition by exhausting the received air from an annular aperture of the air chamber that circumscribes the needle.

9. The apparatus of claim 1, wherein the nozzle assembly further includes:
   a needle centering body, the needle disposed in the needle centering body; and
   a chamber coupled to the needle centering body, the chamber having an inlet in fluid communication with the atomizer and capable of receiving gas from the atomizer for atomizing the composition as the composition is dispensed from the needle on to a stent.

10. A stent coating apparatus, comprising:
    a stent coating composition reservoir containing a stent coating composition;
    a pump capable of dispensing the stent coating composition from the reservoir;
    an atomizer capable of atomizing the stent coating composition; and
    a nozzle assembly in communication with the atomizer, the nozzle assembly having a needle in fluid communication with the reservoir for dispensing the stent coating composition onto a stent from the reservoir,
    wherein the nozzle assembly further includes:
       a needle centering body, the needle disposed in the needle centering body;
       a chamber coupled to the needle centering body, the chamber having an inlet in fluid communication with the atomizer and capable of receiving gas from the atomizer for atomizing the stent coating composition as the composition is dispensed from the needle on to a stent; and
       a coupling element attached to the needle centering body, the coupling element having an inlet in fluid communication with the pump, and wherein the needle is in fluid communication with the coupling element and receives the coating composition from the coupling element through a hollow interior of the needle.

11. The apparatus of claim 9, wherein an outlet of the needle is disposed outside of the chamber.

12. The apparatus of claim 9, wherein an outlet of the needle is disposed inside of the chamber.

13. The apparatus of claim 9, wherein the needle centering body has a threaded surface that is directly threaded on a threaded surface of the chamber, the threaded surfaces enabling variable positioning of an outlet of the needle relative to an outlet of the chamber.

14. The apparatus of claim 9, wherein the needle is coupled to the needle centering body, the needle centering body and a wall of the chamber defining a cavity between the needle centering body and the wall of the chamber, the cavity is or being in fluid communication with the inlet of the chamber and an outlet of the chamber.

* * * * *